United States Patent [19]

Baus et al.

[11] Patent Number: 5,026,720

[45] Date of Patent: Jun. 25, 1991

[54] 1-HYDROXYAZOLE COMPOUNDS AND FUNGICIDES CONTAINING THESE

[75] Inventors: Ulf Baus, Dossenheim; Wolfgang Reuther, Heidelberg; Gisela Lorenz, Neustadt; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 502,237

[22] Filed: Mar. 30, 1990

[30] Foreign Application Priority Data

May 3, 1989 [DE] Fed. Rep. of Germany ....... 3914632

[51] Int. Cl.$^5$ .................. A01N 43/653; C07D 249/08
[52] U.S. Cl. .................... 514/383; 514/184; 548/161; 548/262.2
[58] Field of Search ............. 548/101, 262.2; 514/184, 383

[56] References Cited

U.S. PATENT DOCUMENTS 4,153,399 8/1989 Hubele .............. 548/268.8

Primary Examiner—Mary C. Lee
Assistant Examiner—Patricia L. Morris
Attorney, Agent, or Firm—Oblon, spivak, McClelland, Maier & Neustadt

[57] ABSTRACT

Compounds of the general formula I

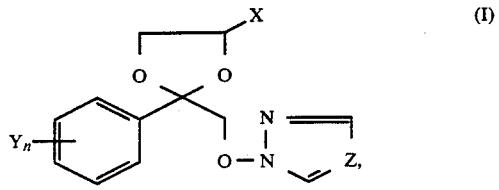

where X is alkyl, aryl, aryloxy or alkoxy, Y is hydrogen, alkyl, alkoxy, halogen, aryl or aryloxy, n is 0 to 5, and Z is CH or N, and fungicides containing these compounds.

5 Claims, No Drawings

1-HYDROXYAZOLE COMPOUNDS AND FUNGICIDES CONTAINING THESE

The present invention relates to novel N-hydroxyazole derivatives, the salts and metal complexes thereof, a process for the preparation thereof, and the use thereof as fungicides.

We have found that compounds of the general formula I

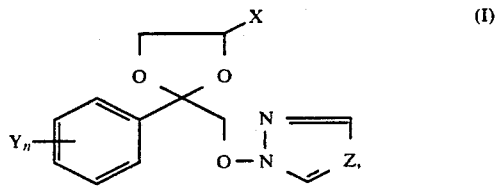

where
- X is alkyl of 1 to 9 carbon atoms, alkoxy, aryloxy, or aryl which can be substituted by halogen, phenyl, aryloxy or alkoxy,
- Y is hydrogen, alkyl, alkoxy, halogen, aryl or aryloxy,
- n is 0 to 5 and
- Z is CH or N and their acid addition salts and metal complexes which are tolerated by plants have a surprisingly good fungicidal action.

Examples of X are $C_1$–$C_9$-alkyl, especially $C_1$–$C_4$-alkyl (methyl, ethyl, tert-butyl, pentyl, hexyl, heptyl, octyl, nonyl), $C_1$–$C_4$-alkoxy (methoxy, ethoxy, tert-butoxy), halogen (Cl, Br, F), aryloxy (phenoxy) or aryl (phenyl), which can be substituted 1 to 5 times (1 to 3 times) by identical or different halogen (fluorine, chlorine, bromine), phenyl, aryloxy (phenoxy), alkoxy of 1 to 4 carbon atoms (methoxy, ethoxy, propoxy), e.g. 4-chlorophenyl, 2,4-dichlorophenyl, 3-methoxyphenyl, 4-chloro-2-methylphenyl and 2,6-dimethylphenyl.

Examples of Y are $C_1$–$C_4$-alkyl (methyl, ethyl, propyl), $C_1$–$C_4$-alkoxy (methoxy, ethoxy), halogen (fluorine, chlorine, bromine), aryl (phenyl) and aryloxy (phenoxy).

n is 0, 1, 2, 3, 4 or 5, and when n is greater than 1 the Y radicals can be identical or different, e.g. 2,4-dichloro- or 4-chloro-2-methyl-.

Examples of salts are the acid addition salts tolerated by plants, e.g. salts with inorganic or organic acids such as the salts of hydrochloric acid, hydrobromic acid, nitric acid, oxalic acid, acetic acid, sulfuric acid, phosphoric acid or dodecylbenzenesulfonic acid. The activity of these salts derives from the cation, so that the choice of the anion is generally arbitrary.

The compounds of the formula I can also be converted by conventional methods into metal complexes. This can be carried out by reacting these compounds with metal salts, e.g. salts of copper, zinc, iron, manganese or nickel, for example copper(II) chloride, zinc(II) chloride, iron(III) chloride, copper(II) nitrate, manganese (II) chloride or nickel(II) bromide.

We have also found that the compounds of the general formula I can be prepared very easily and in good yields by reacting 1-hydroxyazoles with compounds of the general formula II

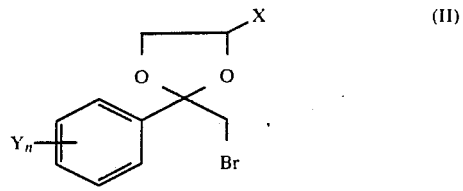

where X, Y and n have the meanings specified for formula I. The compounds of the general formula II are known or can be prepared by known processes (e.g. DE-A 2 551 560).

1-Hydroxy-1,2,4-triazole can be prepared as follows:
103.5 g (1.5 mol) of 1H-1,2,4-triazole were dissolved in 1344 g (12 mol) of 50% strength aqueous potassium hydroxide. While cooling in ice, 340 g (3 mol) of 30% strength $H_2O_2$ and, a little at a time, 555 g (3.75 mol) of phthalic anhydride were added, and the mixture was stirred at room temperature (20° to 30° C.) for 2 hours. It was then acidified with approx. 35% strength sulfuric acid to a pH below 1.5, the resulting precipitate was filtered off with suction, and the filtrate was worked up as usual. 19 g of 1-hydroxy-1,2,4-triazole of melting point 132° C. were obtained. This is a yield of 15% of theory.

The reactions are carried out, for example, in an inert organic solvent such as tetrahydrofuran, dimethyl sulfoxide, dimethylformamide or diethyl ether, preferably dimethylformamide, in the presence of a base such as triethylamine, tributylamine, NaOH, sodium carbonate or pyridine at from 0° to 200° C., preferably at 150° C. It is more advantageous, before adding the bromine compound, to convert the 1-hydroxyazoles in a conventional manner into an alkali metal derivative, e.g. by use of bases such as butyllithium or NaOH/molecular sieves or sodium methylate. Addition of a catalytic amount of an alkali metal iodide has proven advantageous in the reaction. Preparation example 2.55 g of KOH (88% pure) were added to 3.4 g (40 mmol) of 1-hydroxy-1,2,4-triazole in dimethylformamide. The water produced in the reaction was removed with ethanol in a rotary evaporator. 60 ml of DMF and a spatula tip of NaI were added. Then, while stirring, 12.8 g (40 mmol) of 2-bromo-1-(2,4-dichlorophenyl)-1-(4-ethyl-1,3-dioxolan-2-yl)ethane were added, and the solution was heated at 160° C. for 5 h. After the reaction was complete, the DMF was removed in a rotary evaporator, and the residue was taken up in toluene and washed with water. The toluene phase was dried, and the solvent was removed, resulting in 9.7 g (70%) of a viscous oil which was purified by column chromatography (Compound No. 1).

Analysis: $C_{14}H_{15}Cl_2N_3O_3$ (344.19): calc.: C 48.8; H 4.4; Cl 20.6; N 12.2. found: C 49.2; H 4.7; Cl 20.1; N 12.6.

The following were obtained in a corresponding manner:

| No. | X      | Y       | Z  | n | Phys. data |
|-----|--------|---------|----|---|------------|
| 1   | ethyl  | 2,4-DiCl| N  | 2 | oil        |
| 2   | propyl | 2,4-DiCl| N  | 2 | oil        |
| 3   | methyl | 2,4-DiCl| N  | 2 | oil        |
| 4   | propyl | 2,4-DiCl| CH | 2 | oil        |
| 5   | ethyl  | 2,4-DiCl| CH | 2 | oil        |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in vegetables and fruit.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials (wood), for example against Paecilomyces variotii. For treating seed, active ingredient amounts of from 0.001 to 50, preferably 0.01 to 10, g per kg of seed are generally required.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

EXAMPLES OF FORMULATIONS ARE GIVEN BELOW

I. 90 parts by weight of compound no. 1 is mixed with 10 parts by weight of N-methyl-α-pyrrolidone. A mixture is obtained which is suitable for application in the form of very fine drops.

II. 20 parts by weight of compound no. 1 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 2 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 2 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 1 is intimately mixed with 97 parts by weight of particulate kaolin. A dust is obtained containing 3% by weight of the active ingredient.

VII. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 1 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 2 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

USE EXAMPLE

Action on *Pyricularia oryzae* (protective)

Leaves of pot-grown rice seedlings of the "Bahia" variety were sprayed to runoff with aqueous emulsions containing (dry basis) 80% of active ingredient and 20% of emulsifier, and inoculated 24 hours later with an aqueous spore suspension of *Pyricularia oryzae*. The plants were then set up in a climatic cabinet at 22°-24° C. and a relative humidity of 95-99%. The extent of fungus spread was determined after 6 days.

The results show that active ingredient 2, applied as a 0.05 wt % spray liquor, had a good fungicidal action (90%).

We claim:

1. A compound of the formula I

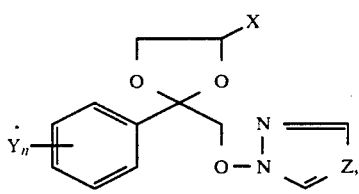

where X is alkyl of 1 to 9 carbon atoms, alkoxy of 1 to 4 carbon atoms, phenoxy, phenyl or phenyl substituted 1 to 5 times by identical or different substituents selected from the group consisting of halogen, phenyl, phenoxy and alkoxy of 1 to 4 carbon atoms, Y is hydrogen, alkyl of 1 to 4 carbon atoms, alkoxy of 1 to 4 carbon atoms, halogen, phenyl or phenoxy, n is an integer from 0 to 5, and Z is N, and their acid addition salts and metal complexes which are tolerated by plants.

2. A compound of the formula I as set forth in claim 1, where X is ethyl, Y is 2,4-dichloro, Z is N and n is 2.

3. A compound of the formula I as set forth in claim 1, where X is propyl, Y is 2,4-dichloro, Z is N and n is 2.

4. A fungicidal composition containing a carrier and fungicidally effective amount of a compound of the formula

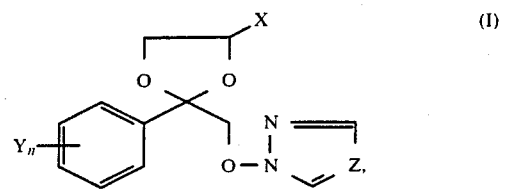

where X is alkyl of 1 to 9 carbon atoms, alkoxy of 1 to 4 carbon atoms, phenoxy, phenyl or phenyl substituted 1 to 5 times by identical or different substituents selected from the group consisting of halogen, phenyl, phenoxy and alkoxy of 1 to 4 carbon atoms, Y is hydrogen, alkyl of 1 to 4 carbon atoms, alkoxy of 1 to 4 carbon atoms, halogen, phenyl or phenoxy, n is an integer from 0 to 5, and Z is N, or an acid addition salt or metal complex thereof which is tolerated by plants.

5. A process for combating fungi, comprising administering a fungicidally effective amount of a compound of the formula

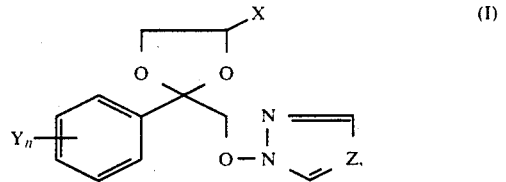

where X is alkyl of 1 to 9 carbon atoms, alkoxy of 1 to 4 carbon atoms, phenoxy, phenyl or phenyl substituted 1 to 5 times by identical or different substituents selected from the group consisting of halogen, phenyl, phenoxy and alkoxy of 1 to 4 carbon atoms, Y is hydrogen, alkyl of 1 to 4 carbon atoms, alkoxy of 1 to 4 carbon atoms, halogen, phenyl or phenoxy, n is an integer from 0 to 5, and Z is N, or an acid addition salt or metal complex thereof which is tolerated by plants, to the fungi, or the plants, seed or wood threatened by fungus attack, or on the soil.

* * * * *